United States Patent [19]
Constancis et al.

[11] Patent Number: 5,646,239
[45] Date of Patent: Jul. 8, 1997

[54] ORGANIC PRODUCTS CONTAINING REACTIVE THIOL FUNCTIONS, ONE METHOD FOR PREPARING SAME, AND BIOMATERIALS CONTAINING SAID PRODUCTS

[75] Inventors: Alain Constancis, Lyons; Gérard Soula, Meyzieu, both of France

[73] Assignee: Flamel Technologies, France

[21] Appl. No.: 578,539

[22] PCT Filed: Jul. 21, 1994

[86] PCT No.: PCT/FR94/00914

§ 371 Date: Mar. 6, 1996

§ 102(e) Date: Mar. 6, 1996

[87] PCT Pub. No.: WO95/03272

PCT Pub. Date: Feb. 2, 1995

[30] Foreign Application Priority Data

Jul. 21, 1993 [FR] France ................................. 93 09198

[51] Int. Cl.$^6$ ................................................ C08G 75/00
[52] U.S. Cl. ............................................................ 528/373
[58] Field of Search ............................................ 528/373

[56] References Cited

FOREIGN PATENT DOCUMENTS

| 0 332 530 | 9/1989 | European Pat. Off. . |
| 1 441 235 | 4/1966 | France . |
| 2 159 183 | 6/1973 | France . |
| 2 274 605 | 1/1976 | France . |

*Primary Examiner*—Terressa Mosley
*Attorney, Agent, or Firm*—Bacon & Thomas

[57] ABSTRACT

The present invention relates to novel organic products resulting, for example, from the condensation of a dicarboxylic acid with a sulfur-containing amino acid or one of its derivatives. These products contain reactive thiol SH functions which can be oxidized to form disulfide bridges, resulting in polymers, which may or may not be crosslinked.

These novel organic products correspond to the following formula:

$$R_3-S-(CH_2)_x-\underset{\underset{R_1}{\overset{|}{C=O}}}{CH}-NH-\overset{O}{\underset{\|}{C}}-R-\overset{O}{\underset{\|}{C}}-NH-\underset{\underset{R_2}{\overset{|}{C=O}}}{CH}-(CH_2)_y-S-R_4 \quad (I)$$

The invention also relates to the polymers and/or networks deriving from the products of formula (I) and to one of the methods for obtaining these products and their derivatives.

Applications as biomaterials: sutures, ligatures, prostheses, adhesives or systems for the controlled release of active principles.

43 Claims, No Drawings

ORGANIC PRODUCTS CONTAINING REACTIVE THIOL FUNCTIONS, ONE METHOD FOR PREPARING SAME, AND BIOMATERIALS CONTAINING SAID PRODUCTS

TECHNICAL FIELD

The present invention relates to novel organic products resulting, for example, from the condensation of a dicarboxylic acid with a sulfur-containing amino acid or one of its derivatives. These products contain reactive thiol SH functions which can be oxidized to form disulfide bridges, resulting in polymers, which may or may not be crosslinked.

PRIOR ART

One of the applications targeted by the invention is the employment of these novel organic products and/or of these optionally crosslinked polymers as biomaterials. These products could, for example, be used as starting materials for the preparation of systems for the controlled release of active principles, of biological adhesives, of sutures, of ligatures, of surgical prostheses or other exogenous structures capable of substituting, at least partially, for the functions, in particular physical or mechanical, of organs and tissues.

Synthetic biodegradable oligomers and polymers are already known which are composed, very often, of simple and hydrolysable chains (esters or amides) of compounds capable of forming metabolites.

Thus, Patent Application EP 0,332,530 describes hydrophilic polymers, with a degree of polymerization of less than 1 000 and preferably of between 20 and 300, composed of polyamides resulting from the condensation of citric acid with diamines, such as lysine, cystamine or cystinc.

The synthesis of these polyamides presents real difficulties related to the protection and then to the deprotection of the citric acid.

These biodegradable polyamides can be used for the preparation of medicinal vehicles, of sutures, of ligatures or of prostheses or alternatively of surgical adhesives.

If, in certain applications, the use of polymers of relatively high mass, of the type of those described in Patent Application EP 0,332,530, is advantageous, the employment of monomers or of oligomers carrying reactive or polymerizable functions (prepolymers) is preferable for other uses. This is the case, in particular, in restorative surgery (bone filler, surgical cements, biological adhesives, and the like) or in dental surgery (dental cements, and the like). In these applications, it is advantageous for the monomer or prepolymer to be able to diffuse very easily into the tissue to be repaired and thus to penetrate into all the cavities. Polymerization can then take place "in situ" and give rise to an intermeshing of polymer chains having the desired filling, cohesive or adhesive properties.

In this state of the art, one of the essential objectives of the invention is to provide organic synthetic products which can, in particular, be used as the basis for the preparation of non-toxic, biocompatible and biofunctional biomaterials which are useful, inter alia, as systems for the controlled release of active principles, sutures, ligatures, surgical adhesives or alternatively as surgical prostheses or implants.

Another essential objective of the invention is to provide organic synthetic products which are in the form of prepolymers and/or of monomers capable of easily diffusing into biological tissues and of polymerizing in situ, indeed in vivo, to satisfactorily provide for the functions of filling, of reinforcing cohesion or of adhesion.

STATEMENT OF THE INVENTION

These objectives and others are achieved by the present invention which relates, in the first place, to a novel organic product containing at least two thiol or derived functions and/or carboxyl functions, which may or may not be protected, and/or carbonyl functions, of following general formula:

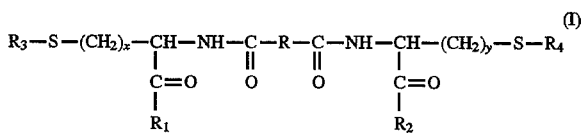

in which:

R is a hydrocarbon chain, preferably an alkyl chain containing from 1 to 50 carbon atoms and, more preferentially still, an aliphatic chain having from 1 to 10 carbon atoms, $R_1$ and $R_2$ are identical or different and are chosen from the following groups:

$-O-R_5$;

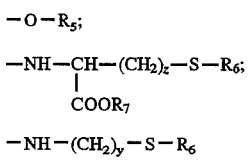

$-NH-(CH_2)_y-S-R_6$ $R_3$, $R_4$, $R_5$, $R_6$ and $R_7$ independently represent hydrogen or an aliphatic and/or alicyclic and/or aromatic group, preferably a lower alkyl group and/or an aromatic group and, more preferentially still, one of the following groups:

$-CH_3$;

$-CH_2CH_3$;

$-CH_2-Phe$;

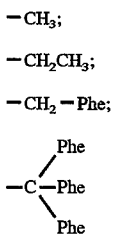

x, y and z=1 or 2, with the exception of the products of formula (I) in which:

R=—$(CH_2)_t$, with t=2, 4 or 6 to 12, $R_1$ and $R_2$ are identical and correspond to OH, —O-alkyl, —$NH_2$ or —N-alkyl, $R_3$ and $R_4$ are identical and represent hydrogen, —$CH_3$ or —$CH_2$—COOH, x and y are identical and are equal to 1 or 2.

For reasons of simplification, the aromatic rings are denoted by Phe throughout the present statement.

Within the meaning of the present invention, the term "lower alkyl" denotes radicals comprising from 1 to 6 carbon atoms.

BETTER WAY OF PRODUCING THE INVENTION

The biological compounds corresponding to this formula advantageously have a relatively low molecular mass (less than 2 000) and can therefore rapidly and easily diffuse through the networks of proteins (collagen, elastin, and the like) or glycoproteins of which tissues are composed. This is a property which it is advantageous to exploit in the field of adhesives.

A first subgroup of the products of the invention comprises those in which the $R_1$ and $R_2$ radicals represent $OR_5$.

More precisely still, as soon as $R_3$ and $R_4$ correspond to hydrogen, there is present an oligomer having, at each of its two ends, an SH function carded by a cysteine or derived unit ("di-SH" oligomer).

These SH functions have the property of being able to react with each other, to form disulfide bridges and to make it possible to obtain long chains. This property can be exploited in order to prepare biodegradable yarns, films or viscous solutions.

The presence of carboxyl functions on these di-SH compounds makes it possible to envisage interactions with other molecules (for example natural macromolecules). This tends to improve the adhesive properties. In addition, these carboxyl functions bring about a hydrophilic nature and an ability to attach active principles.

A second typical subgroup of the products in accordance with the invention combine the products corresponding to the abovementioned general formula, in which the $R_1$ radical represents:

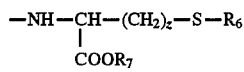

and $R_2$ represents —O—$R_5$, or vice versa.

As soon as $R_5$ and $R_6$ consist of hydrogen, these compounds may be described as "tri-SH" oligomers. These oligomers, the SH ends of which are capable of reacting in order to form disulfide bridges, allow possibilities of the development of multidirectional networks to be anticipated, which networks can only improve the mechanical properties, the adhesive powers and the resistance to biodegradation of the products according to the invention.

A third subgroup of organic products according to the invention consists of the products in which the $R_1$ and $R_2$ radicals consist of the radical:

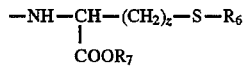

With $R_3$, $R_4$ and $R_6$ corresponding to hydrogen, a tetrafunctional oligomer is defined which contains four SH units at its ends ("tetra-SH" oligomer). This multiplicity of potential anchoring points can advantageously be exploited in the field of biomaterials. This comes within the continuation of that which was shown above for the di- and trifunctional oligomers.

The cysteine unit used can be formed by cysteine itself: x, y and z=1, or by homocysteine: x, y, z=2, which can optionally result from cystine or homocystine.

The alkyl chain R, which is optionally substituted, defines the radical:

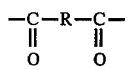

in the formula (I), so that it belongs to the group of residues of poly-, advantageously di-, carboxylic acids, with the exception of citric acid, R preferably being selected from the following groups:

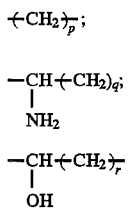

with:

$p \leq 5$, preferably equal to 2 (succinic acid) or to 3 (glutaric acid), $q \leq 5$, preferably equal to 1 (aspartic acid) or to 2 (glutamic acid), and, finally, $r \leq 5$, preferably equal to 1 (malic acid).

R can also be composed of low molecular mass polylactic and/or polyglycolic and/or poly(amino acid) chains.

These oligomers in accordance with the invention are carriers of SH functions which confer on them abilities to polymerize and/or to crosslink, optionally in the presence of an oxidizing agent. They therefore make it possible to obtain, after oxidation, polymers, which may or may not be crosslinked, which can be used as biomaterials and which are optionally degradable to natural metabolites, i.e. which are involved in the biological cycles of mammals.

Moreover, their size and their structure are such that they can easily migrate and penetrate into biological tissues.

It follows that these oligomers can without difficulty reach the targeted biological sites and can polymerize "in situ" so as to form an intermeshing and/or a network of polymer chains.

These oligomers therefore find outlets as constituents of products for restorative surgery (bone filler, surgical cements, biological adhesives, and the like) or for dental surgery (dental cements, and the like) where their filling, reinforcing of cohesion or adhesive properties are exploited.

These properties can also be of advantage in another field of application which is that of the bioadhesive forms used in certain systems for the controlled release of therapeutic active principles. In certain applications, it is preferable to employ a liquid form, because this facilitates the application of the active principle/prepolymer unit, and then the formation of a polymer matrix in situ in contact with the mucous membrane (in the presence or in the absence of an oxidizing agent which triggers polymerization) makes possible the controlled release of the active principle. Such systems are particularly advantageous in the treatment of local complaints.

Moreover, polymerization of the products according to the invention by oxidation of the SH groups to disulfide bridges can also be carried out in vitro and thus can make possible the formation of moldable films or objects which can be used as biomaterials.

The present invention also relates to polymers capable of being obtained from the oligomers, as described above, and which correspond to the following general formula:

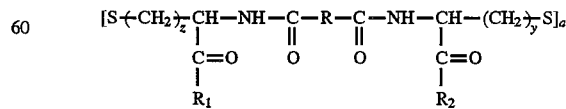

in which:

$R_1$ and $R_2$ are identical or different and are chosen from the following groups:

—O—R$_5$;

—NH—CH—(CH$_2$)$_x$—S—R$_6$;
  |
  COOR$_7$

—NH—CH$_2$—CH$_2$—S—R$_6$;

with R$_5$, R$_6$ and R$_7$ independently representing hydrogen or an aliphatic and/or alicyclic and/or aromatic group, preferably a lower alkyl group and/or an aromatic group and, more preferentially still, one of the following groups:

—CH$_3$;

—CH$_2$CH$_3$;

—CH$_2$—Phe;

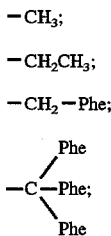

R is chosen so that the radical:

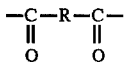

of the formula (I) is a radical belonging to the group of poly-, advantageously di-, carboxylic acids, with the exception of citric acid, R preferably being selected from the following groups:

—(CH$_2$)$_p$—;

—CH—(CH$_2$)$_q$;
  |
  NH$_2$

—CH—(CH$_2$)$_r$;
  |
  OH with:
p≦5, preferably equal to 2 or 3,
q≦5, preferably equal to 1 or 2,
and r≦5, preferably equal to 1,
n being between 1 and 100, preferably between 2 and 50 and, more preferentially still, between 4 and 30, and x and y corresponding to 1 or 2, as above.

R can also be composed of low molecular mass polylactic and/or polyglycolic and/or poly(amino acid) chains.

These polymers are polysulfides in which the repeat unit preferably results from the combination of succinic acid and of cysteine.

These polymers can be used as the basis for preparing other novel products in accordance with the invention which consist of networks (III). This crosslinking is carried out, for example, by amidation and/or esterification, using at least one bridging agent, preferably chosen from polyols and/or polyamides and, more preferentially still, from the following products: cystine, lysine, cystamine and their derivatives, aldoses and ketoses and their hydrogenated derivatives and other polyols (glycerol).

The invention relates, as novel products, to the networks III crosslinked by bridges resulting from at least one bridging agent of the type of that mentioned above.

Given that all the products in accordance with the invention described above can be fitted into the same preparation sequence, it is clear that the present invention also relates to any composition composed of a mixture of at least two of the abovesaid products.

The products according to the invention are biocompatible and have proved to be particularly appropriate for taking part in the composition of biomaterials.

Another subject of the present invention is thus any material formed by a mixture and/or by a formulation of at least one of the oligomers (I) and/or polymers (II) and/or networks (III) and/or compositions described above with biological macromolecules or biodegradable synthetic or natural polymers, such as:

polysaccharides; e.g. starch, cellulose, chitosan, dextran or mucopolysaccharides, such as hyaluronic acid or chondroitin sulfate;

proteins; e.g. collagen, gelatin, albumins or globulins;

poly(amino acid)s;

polyesters (in particular lactic and/or glycolic polyesters), polyorthoesters, polyanhydrides or polyphosphazenes;

and lipids and phospholipids.

The preparation of the products I, II and III according to the invention fits into a reaction scheme in which the first stage is the preparation of polymers, including in particular those corresponding to the formula II, which then give access to the products I, which themselves can be reconverted to polymers II or to networks III.

According to a preferred embodiment of the invention, this preparation consists in carrying out:

a) a polycondensation between:
on the one hand, a reactant of formula A:

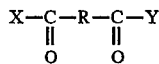

with X and Y, which are identical or different, representing a halogen, preferably chlorine, or an —OR$_8$ radical, in which R$_8$ corresponds to hydrogen or to an alicyclic or aliphatic radical, preferably chosen from the list of the following radicals:

O
||
—C—C(CH$_3$)$_3$;

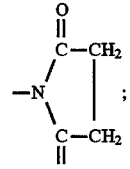

—C—C$_2$H$_5$
||
O and with an R radical which is a hydrocarbon chain, preferably an alkyl chain, containing from 1 to 50 carbon atoms and, more preferably still, an aliphatic chain having from 1 to 10 carbon atoms, and, on the other hand, a reactant of formula B:

R$_9$HN—CH—(CH$_2$)$_x$—S—S—(CH$_2$)$_y$—CH—NHR$_{10}$
         |                                    |
         COOR$_1$                              COOR$_2$ with R$_1$ and R$_2$ corresponding to a definition identical to that given above, with R$_9$ and R$_{10}$, which are identical or different, chosen from the following radicals: H or aliphatic, preferably alkyl, hydrogen additionally being that which is more preferentially retained, and with x and y classically being equal to 1 or 2, b) a reduction of the polymer obtained, which may or may not be subsequently converted.

In practice, it is preferable for the compound of formula A to be in the form of an acid halide, for example an acid chloride, and for the compound B of cysteine nature to be esterified with $R_1$ and $R_2$ alkyl radicals preferably consisting of methyl radicals.

Two polycondensation techniques can be envisaged for producing polymers, including those of formula II: solution polycondensation or interfacial polycondensation.

These techniques will be viewed in detail in the examples below.

Once the polymer has been obtained, it is advantageous to hydrolyze the ester functions carded by this polymer. This hydrolysis is carried out in water, in mild alkaline medium, in order to conserve the functions other than the ester functions of the polymer (saponification).

According to a first alternative form of the process in accordance with the invention, the polymer, which may or may not have been subjected to hydrolysis of its ester functions, is subjected to a reduction b) of the disulfide bridges which it contains, which makes it possible to obtain mostly difunctional oligomers carrying an SH unit at each of their ends.

The reduction techniques used are conventional. They may be, for example, those described in Methods in Enzymology, vol. 143, "Sulfur and sulfur amino-acids", W. B. Jakoby and O. W. Griffith, Academic Press Inc., Orlando, (1987).

According to a second alternative form of the process according to the invention, the partially or completely saponified polymer is subjected to crosslinking. This polymer can be the polycondensate as is or the polycondensate reduced in accordance with the first alternative form of the process according to the invention, which corresponds to the di-SH difunctional oligomers. The crosslinking takes place via at least one bridging agent and, preferably, in the presence of a coupling agent.

The bridging agent is, preferably, a diol or a diamine having at least one —S—S— bond, such as, for example, cystinc dialkyl esther [sic](methyl or ethyl).

The coupling agent is advantageously chosen from the list of following compounds: ethyl(diaminopropyl) carbodiimide (EDC) or carbonyldiimidazole (CDI).

It is possible to change the degree of crosslinking by varying the amount of bridging agent used, with respect to the number of acid functions of the polymer.

The concentration of bridging agent is defined by the following ratio:

According to the invention, this ratio is between 0.01 and 1.

$$\frac{\text{number of NH}_2 \text{ or OH functions or the like of the bridging agent}}{\text{number of COOH functions of the polymer}}$$

The networks III obtained can be symbolized as follows:

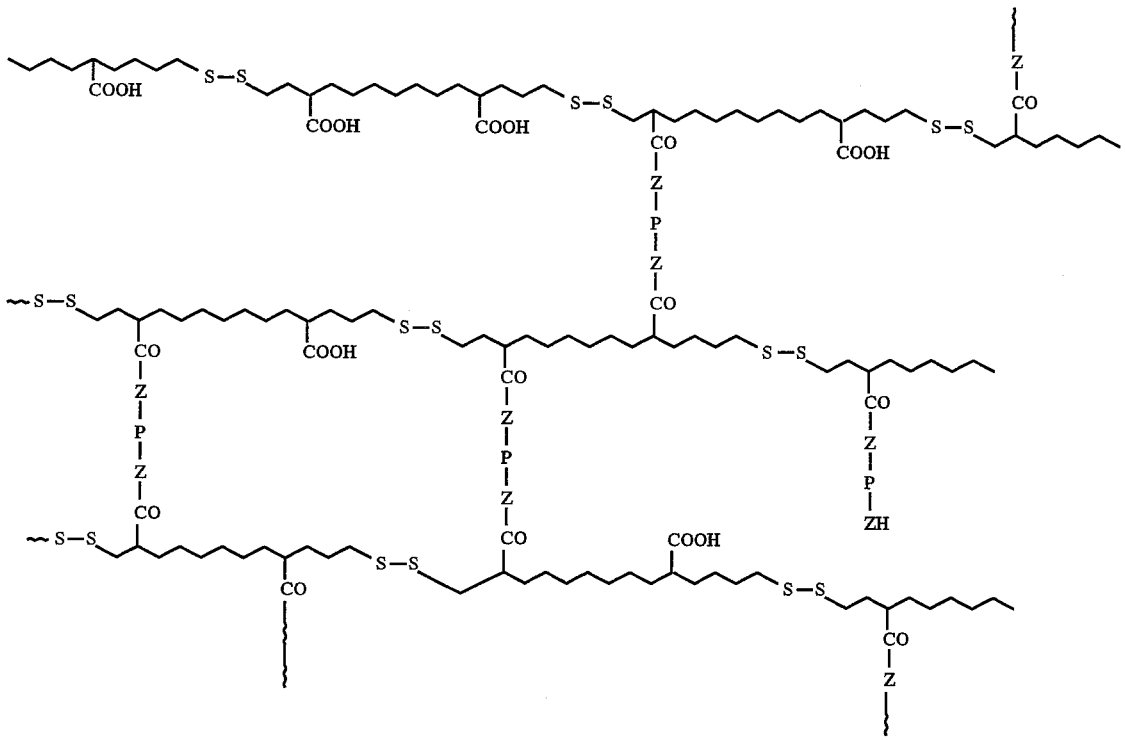

with Z=O or NH.

—Z—P—Z— is a bridge deriving from the polyols (Z=0[sic]): HO—P—OH or from the polyamides (Z=NH): $H_2N$—P—$NH_2$.

The reduction of such a network can be carded out in suspension in water in the presence of dithiothreitol or of tributylphosphine. It results in a mixture of molecules containing a number of-SH functions which can be isolated, lyophilized and stored under nitrogen at a temperature below 0° C. It is then possible, under mild oxidation conditions, to reform the disulfide bridges in order to obtain a network similar to (iii).

In the specific case where the bridging agent is chosen from the following products: cystamine or esters of cystine or of homocystine, the groups P of the network (III) also contain disulfide bridges and the reduction of the network then results in a mixture mostly composed of the di-, tri- and tetra-SH molecules described above (formula I).

The last stage of the process in accordance with the invention, common to both the alternative forms mentioned above, consists in oxidizing the SH oligomers obtained in the preceding stage, so as to produce polymers, including in particular those of formula (II), and/or networks (III), disulfide bridges being (re)formed.

This oxidation is carried out either, and preferably, in the presence of at least one oxidizing system comprising, for example, iodine and/or its derivatives and/or hydrogen peroxide, or by electrochemistry or directly in air.

The present invention is also targeted at any composition formed by a mixture of at least two products of formula I and/or II and/or III.

In particular, the advantageous compositions are those comprising mixtures of oligomers I because, once reoxidized, the latter result in multi-SH coatings, gels or biomaterials described above. These reoxidized compounds must exhibit a number of mechanical properties, in correspondence with their characteristics of use. The level of the mechanical properties is essentially dependent on the structure of the network formed and on the control of the crosslinking of the multifunctions, preferably multi-SH functions, of the oligomers. In theory, any multi-SH composition with a mean SH functionality strictly greater than 2 can give an insoluble network. The mean SH functionality may be defined as follows:

$$F_{mean} = \text{number of SH units per molecule} = \frac{A}{B}$$

with:
A=1. number of mono-SH molecules +2. number of di-SH molecules +3. number of tri-SH molecules +4. number tetra-SH molecules,
B=number of mono-SH molecules+number of di-SH molecules+number of tri-SH molecules+number of tetra-SH molecules.

Taking into account the possibility of intramolecular reactions which disturb the formation of the network by consuming potential nodes, it is preferable to target $F_{mean}$ values for the mixtures of oligomers of the order of 2.1 to 2.5, in order to ensure formation of the network. Generally, the elasticity and the swelling (gel appearance) of the network decreases when the $F_{mean}$ increases.

A desired mean functionality (for example 2.3) can be obtained directly or indirectly.

According to the direct method, the crosslinking is carried out of linear polycondensates of known length, in order to estimate the relative proportion of mono-SH with respect to the di-SH units, with a suitable amount of bridging agent, such as cystine dimethyl ester. After reduction of the network obtained, there is available a mixture of mono-, di-, tri- and tetra-SH in which the $F_{mean}$ will be close to that desired. It is necessary, however, to make sure of the total reactivity of the bridging agent and of the totality of the reduction of the SS bridges.

The indirect method consists in "overcrosslinking" a linear polymer by targeting a theoretical $F_{mean}$ in the region of 3 for example, in reducing this network, in determining by quantitative determination the Frocan obtained, in preparing, by reduction of a linear polycondensate, the mixture of mono- and of di- SH close to 2 and in obtaining, by mixing the two quantitatively determined compositions in desired proportions, in order to obtain [sic] the $F_{mean}$ corresponding to an optimum for the desired properties.

For applications of biomaterials requiring formation of a gel, it appears desirable to start from a composition, i.e. from a mixture of oligomers, having an $F_{mean}$ greater than or equal to 2, preferably less than or equal to 2.6 and, more preferentially still, less or equal to 2.3.

For harder items, filler cements, osteosynthesis components or rigid implants, it appears desirable to target $F_{mean}$ values greater than or equal to 2.3 and, preferentially, greater than or equal to 2.5.

The oligomers (I), polymers (II) inter alia or networks (III), which may or may not be functionalized, in accordance with the invention are compounds exhibiting no direct or indirect toxicity: they are not carcinogenic, teratogenic, immunogenic or mutagenic. Moreover, they are entirely biodegradable, that is to say that they consist of products which fit perfectly well into the metabolic routes (Krebs cycle in particular) of the human being or animal. The degradation products of these compounds are ipso facto fully tolerated.

POSSIBILITY OF INDUSTRIAL APPLICATION

The products in accordance with the invention find advantageous applications as a biomaterial, which can, for example, be used as the basis for the manufacture of sutures, of ligatures, of vascular, osseous, tissue or ligamentous surgical prostheses, of implants of any nature or alternatively of a system for the controlled release of active principles.

In particular, it is advantageous to note that the oligomers (I) according to the invention have a low molar mass (less than 1000 Da) and that they are thus capable of diffusing within biological tissues in order subsequently to be polymerized and/or crosslinked therein. The intermeshings which they then form with the glycoproteins provide a solid adhesive bond.

In the reduced form and in combination with an oxidizing system, these products and/or their mixtures are highly suitable as constituents of surgical or dental cements, of filler agents or of biological adhesives. These constituents come within the scope of the invention.

In the oxidized form, these constituents are cohesive networks with scattered disulfide bridges having between them adjustable mechanical and biological properties.

The following Examples 1 to 10 are an illustration of the properties and of the alternative structural forms of the products according to the invention. They also describe the structures and the methods of preparation of the products according to the invention.

EXAMPLES

Example 1

Synthesis of the Polymer (1) by Solution Polycondensation in Dimethylacetamide (DMAC) of Cystine Dimethyl Ester Hydrochloride and of Succinyl Chloride.

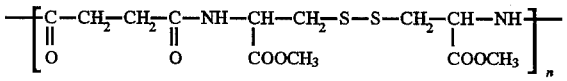

25 g (0.073 mol) of cystine dimethyl ester hydrochloride and 400 ml of DMAC are placed in a 1 l reactor. 41.2 ml of triethylamine (0.293 mol) are then added. 8.1 ml of freshly distilled succinyl chloride are diluted in 100 ml of DMAC and the combination is added to the reaction mixture using a dropping funnel. The reaction mixture is then stirred for 24 hours at room temperature. The precipitated triethylammonium salt is removed by filtration and the reaction mixture is then precipitated from 5 l of water. The polymer is recovered by filtration and dried in an oven under vacuum: 13 g of a white (slightly pink) powder are thus obtained. The $^1$H NMR (in deuterated trifluoroacetic acid (TFA) [sic] and IR spectra are in agreement. The molar masses, determined by steric exclusion chromatography (SEC) in DMAC and expressed in polystyrene equivalents are as follows:

$M_n=6200, M_w=9600$

Example 2

Synthesis of the Polymer (1) by Water/Toluene Interfacial Polycondensation of Cystine Dimethyl Ester Hydrochloride and of Succinyl Chloride.

25 g (0.073 mol) of cystinc dimethyl ester hydrochloride and 200 ml of DMAC are placed in a 1 l reactor. 31.06 g of anhydrous sodium carbonate (0.293 mol) are then added. A preemulsion is then formed by addition of 100 ml of toluene. 8,1 ml of freshly distilled succinyl chloride are then diluted in 100 ml of toluene and the combination is added to the reaction mixture using a dropping funnel. The reaction mixture is then stirred for 4 hours at room temperature. The polymer, precipitated during the reaction, is recovered by filtration and washed with acetone and then with water. It is dried in an oven under vacuum: 14 g of a white (slightly pink) powder are thus obtained. The $^1$H NMR (in TFA) and IR spectra are in agreement and similar to those obtained for the polymer of Example 1. The molar masses, determined by SEC in DMAC and expressed in polystyrene equivalents, are as follows:

$M_n=5700, M_w=11,500$

Example 3

Hydrolysis of the Ester Functions of the Polymer (1): Preparation of the Polymer (2).

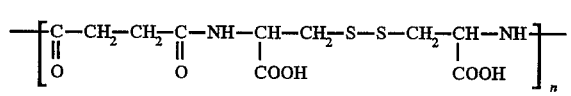

5 g of polymer (1) obtained by solution or interfacial polycondensation are suspended in 1 l of water. The pH is adjusted to 10.5 with 1M sodium hydroxide and maintained at this value throughout the hydrolysis. The addition of sodium hydroxide is halted when the solution has become clear. The solution is then acidified to a pH<3 by an acid ion exchange resin. It is concentrated, frozen and then lyophilized. 4.6 g of white powder are obtained. The $^1$H NMR (in TFA and in D$_2$O) and IR spectra are in agreement and show that all the ester functions are hydrolyzed.

Example 4

Reduction of the Polymer (2) by Dithiothreitol Preparation of the Molecule (3).

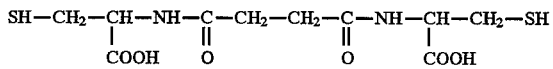

3 g of polymer (2) and 2.87 g of dithiothreitol (DTT) are dissolved in 70 ml of water under a nitrogen atmosphere. The pH is adjusted to 8.5 by addition of 1M sodium hydroxide and the solution is stirred for 3 hours while bubbling nitrogen through. The mixture is then extracted twice with 100 ml of ethyl acetate. The aqueous phase is then acidified by an acid ion exchange resin to pH=4.5 and then concentrated and precipitated from an excess of acetone. The sticky precipitate obtained is redissolved in the minimum amount of water and reprecipitated from acetone. It is finally redissolved in water and lyophilized. 2 g of a slightly yellow product are recovered. The $^1$H NMR spectrum (in D$_2$O) obtained is in accordance with the formula (3), the carboxyl groups being in the ionized form.

Example 5

Reduction of the Polymer (2) by Tri-(N- Butyl) Phosphine [sic]: Preparation of the Molecule (3).

2.4 g of polymer (2) are dissolved in 30 ml of water under a nitrogen atmosphere. 120 ml of methanol, degassed beforehand, are then added. 2ml of tri(n-butyl)phosphine are then injected into the reaction mixture. After reacting for 3 hours, the methanol is evaporated using a rotary evaporator. 50 ml of water are added to the residual aqueous solution which is then extracted twice with 200 ml of ethyl acetate. The aqueous solution is then acidified and precipitated from acetone, as described in Example 4. The $^1$H NMR spectrum in D$_2$O is identical to that of the product obtained in Example 4.

Example 6

Crosslinking of the Polymer (2) by Cystine Dimethyl Ester.

5 g of the polymer (2) and 5.3 g of cystine dimethyl ester hydrochloride are dissolved in 100 ml of water. 6 g of N-dimethylaminopropyl-N'-ethylcarbodiimide (EDC) are then dissolved in 5 ml of water and immediately added to the reaction mixture. The mixture immediately takes on a dark red coloring and then, after a few seconds, a pink precipitate is formed. The reaction is halted after 3 hours and 200 ml of water are added. The precipitate is recovered by filtration, washed a number of times with water and then dried in an oven under vacuum.

Example 7

Crosslinking of the Polymer (2) by Cystine Diethyl Ester.

5 g of the polymer (2) and 5.73 g of cystine diethyl ester hydrochloride are dissolved in 100 ml of water. 6 g of N-dimethylaminopropyl-N'-ethylcarbodiimide (EDC) are then dissolved in 5 ml of water and immediately added to the reaction mixture. The reaction is halted after 3 hours and 200 ml of water are added. The precipitate is recovered by filtration, washed a number of times with water and then dried in an oven under vacuum.

Example 8

Reduction by Dithiothreitol of the Crosslinked Polymer From Example 6.

1 g of the crosslinked polymer from Example 7 and 1.1 g of dithiothreitol are dissolved in 50 ml of water purged beforehand by a stream of nitrogen. The pH is adjusted to 9.5 with 1M sodium hydroxide. The reaction mixture becomes clear and the reaction is halted after 1 hour. After six extractions with 50 ml of ethyl acetate, the aqueous solution is acidified to pH=5 by an exchange resin, reextracted with two times 50 ml of ethyl acetate and then lyophilized. The product obtained is a mixture mainly comprising the following molecules (3), (4) and (5):

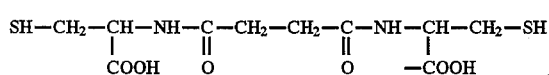
(3)

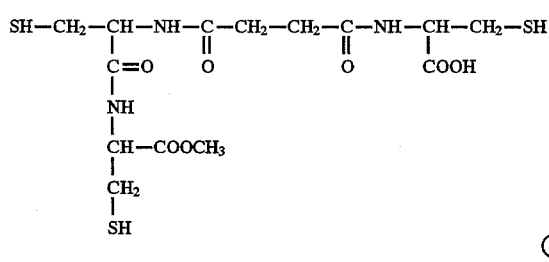
(4)

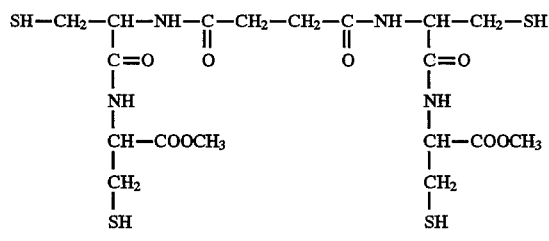
(5)

The carboxyl functions are in the ionized form (—COO⁻ Na⁺). The mixture is no longer completely soluble in water when the pH is <3.

Example 9

Reduction by Dithiothreitol of the Crosslinked Polymer From Example 6-Hydrolysis of the Ester Functions of the Product Obtained.

The reaction is carried out as described in Example 8, but the reduced solution is maintained at pH=9.5 for 24 hours at 35° C. After six extractions with 50 ml of ethyl acetate, the aqueous solution is acidified to pH=5 by an exchange resin, reextracted with two times 50 ml of ethyl acetate and then lyophilized. The product obtained is a mixture mainly comprising the following molecules (3), (6) and (7):

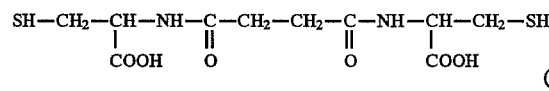
(6)

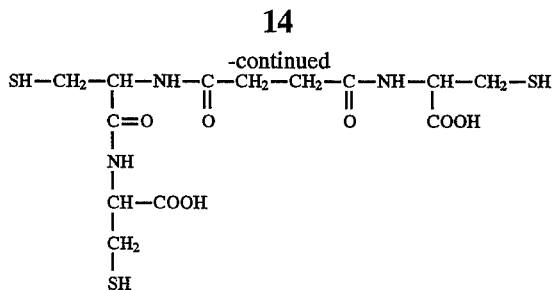
(7)

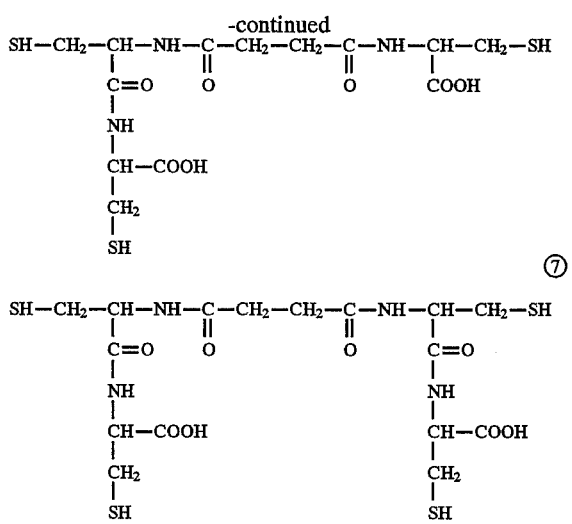

The carboxyl functions are in the ionized form (—COO⁻ Na⁺). The mixture can be acidified (to pH=2.5) by passing through an ion exchange resin. In this case, the solubility in water is retained.

Example 10

Reduction by Dithiothreitol of the Crosslinked Polymer From Example 7.

1 g of the crosslinked polymer from Example 7 and 1.1 g of dithiothreitol are dissolved in 50 ml of water purged beforehand by a stream of nitrogen. The pH is adjusted to 9.5 with 1M sodium hydroxide. The reaction mixture becomes clear and the reaction is halted after one hour. After six extractions with 50 ml of ethyl acetate, the aqueous solution is acidified to pH=4 with a 1N HCl solution. A sticky, slightly brown, precipitate is obtained. It is a mixture mainly composed of the following molecules (3), (8) and (9):

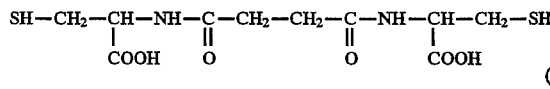
(3)

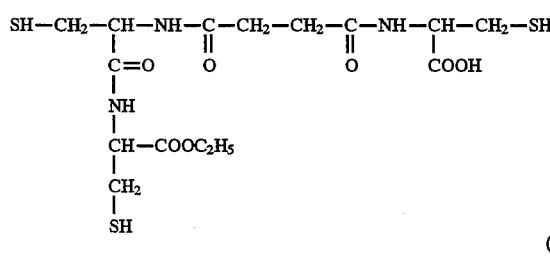
(8)

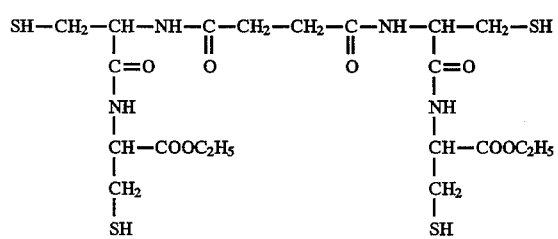
(9)

We claim:
1. Organic product containing at least two thiol or derived functions or carbonyl functions, said organic product having the following general formula:

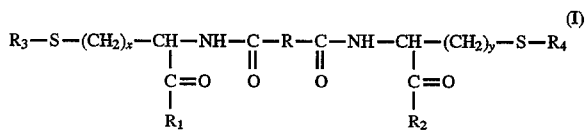

in which:

R is a hydrocarbon chain, $R_1$ and $R_2$ are identical or different and are chosen from the following groups:

—O—$R_5$;

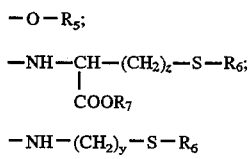

—NH—$(CH_2)_y$—S—$R_6$ $R_3$, $R_4$, $R_5$, $R_6$ and $R_7$ independently represent hydrogen or an aliphatic group, an alicyclic group or an aromatic group, x, y and z=1 or 2, with the exception of the products of formula (I) in which:

R=—$(CH_2)_T$ with T=2, 4 or 6 to 12, $R_1$ and $R_2$ are identical and correspond to OH, —O—alkyl, —$NH_2$ or —N—alkyl, $R_3$ and $R_4$ are identical and represent hydrogen, —$CH_3$ or —$CH_2$—COOH, x and y are identical and are equal to 1 or 2.

2. Product according to claim 1, characterized in that R is an alkyl chain having from 1 to 50 carbon atoms.

3. Product according to claim 1, characterized in that R is an aliphatic chain having from 1 to 10 carbon atoms.

4. Product according to claim 1, characterized in that $R_3$, $R_4$, $R_5$, $R_6$ and $R_7$ independently represent a hydrogen, a lower alkyl group or an aromatic group.

5. Product according to claim 1, characterized in that $R_3$, $R_4$, $R_5$, $R_6$ and $R_7$ independently represent a hydrogen or a group selected from the following:

—$CH_3$; —$CH_2CH_3$; —$CH_2$—Phe; and

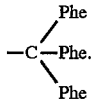

6. Product according to claim 1, characterized in that $R_1$ and $R_2$ represent —O—$R_5$.

7. Product according to claim 1, characterized in that $R_1$ represents:

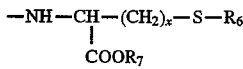

and $R_2$ represents —O—$R_5$, or vice versa.

8. Product according to claim 1, characterized in that $R_1$ and $R_2$ consist of the radical:

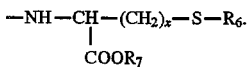

9. Product according to claim 1, characterized in that it is convertible into a polymer by oxidation.

10. Product according to claim 1, characterized in that R is chosen so that the radical:

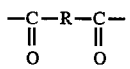

of the formula (I) is a radical belonging to the group of the residues of poly-carboxylic acids, with the exception of citric acid.

11. Product according to claim 10, characterized in that the radical

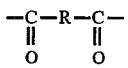

of the formula (I) is a radical belonging to the group of the residues of di-carboxylic acids.

12. Product according to claim 10, characterized in that R is selected from the group consisting of:

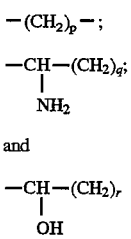

with $p \leq 5$, $q \leq 5$ and $r \leq 5$.

13. Product according to claim 11, characterized in that R is selected from the group consisting of:

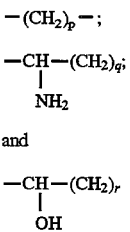

with $p \leq 5$, $q \leq 5$ and $r \leq 5$.

14. Product according to claim 12, characterized in that p=3, q=1 or 2 and r=1.

15. Product according to claim 13, characterized in that p=3, q=1 or 2 and r=1.

16. Product according to claim 1, characterized in that R is composed of low molecular mass chains selected from the group consisting of polylactic, polyglycolic and poly(amino acid) chains.

17. Polymers obtained from the product according to claim 10, of the following general formula:

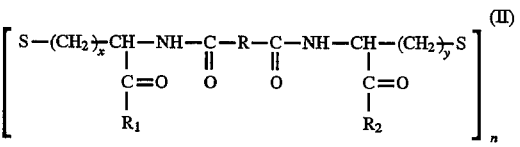

wherein n is between 1 and 100.

18. Polymers obtained from the product according to claim 16, of the following general formula:

$$\left[ \begin{array}{c} S-(CH_2)_x-CH-NH-C-R-C-NH-CH-(CH_2)_y-S \\ | \quad\quad\quad\quad || \quad\quad || \quad\quad\quad\quad | \\ C=O \quad O \quad O \quad C=O \\ | \quad\quad\quad\quad\quad\quad\quad\quad\quad\quad\quad | \\ R_1 \quad\quad\quad\quad\quad\quad\quad\quad\quad R_2 \end{array} \right]_n \quad (II)$$

wherein n is between 1 and 100.

19. Polymers according to claim 17, characterized in that $R_1$ and $R_2$ represent —O—$R_5$.

20. Polymers according to claim 17, characterized in that $R_1$ represents:

$$-NH-CH-(CH_2)_x-S-R_6$$
$$\quad\quad |$$
$$\quad COOR_7$$

and $R_2$ represents —O—$R_5$, or vice versa.

21. Polymers according to claim 17, characterized in that $R_1$ and $R_2$ consist of the radical:

$$-NH-CH-(CH_2)_x-S-R_6.$$
$$\quad\quad |$$
$$\quad COOR_7$$

22. Networks, characterized in that they are composed of polymers according to claim 17 crosslinked by bridges resulting from at least one bridging agent.

23. Networks according to claim 22, characterized in that the bridging agent is selected from the group consisting of polyols and polyamines.

24. Networks according to claim 23, characterized in that the bridging agent is selected from the group consisting of cystinc, cystinc derivatives, lysine, lysine derivatives, aldoses, ketoses, hydrogenated derivatives of aldoses, hydrogenated derivatives of ketoses and polyols.

25. Networks according to claim 24, characterized in that the bridging agent is glycerol.

26. A composition comprising a mixture of at least two of the products according to claim 1.

27. The composition according to claim 26, comprising a mixture of oligomers of formula (I), and having an $F_{mean}$ greater than or equal to 2.

28. Process for the preparation of a product according to claim 1, comprising the following steps:
(a) performing a polycondensation reaction between:
a reactant of formula A:

$$X-C-R-C-Y$$
$$\quad || \quad\quad ||$$
$$\quad O \quad\quad O$$

with X and Y, which are identical or different, representing a halogen, or an —$OR_8$ radical, in which $R_8$ is selected from the group consisting of hydrogen, an aliphatic radical and an alicyclic radical,
and with R in accordance with the definition given in claim 1,
and a reactant of formula B:

$$R_9HN-CH-(CH_2)_x-S-S-(CH_2)_y-CH-NHR_{10}$$
$$\quad\quad | \quad\quad\quad\quad\quad\quad\quad\quad\quad\quad |$$
$$\quad COOR_1 \quad\quad\quad\quad\quad\quad\quad COOR_2$$

with $R_1$ and $R_2$ as defined in claim 1,
with $R_9$ and $R_{10}$, which are identical or different, chosen from the following radicals: H or aliphatic, and with x and y=1 or 2; and (b) performing a reduction of the polymer obtained in step (a).

29. Process according to claim 28, wherein X and Y, which are identical or different, represent a chlorine or an —$OR_8$ radical.

30. Process according to claim 28, wherein $R_9$ and $R_{10}$, which are identical or different, are chosen from H or alkyl.

31. Process according to claim 28, wherein $R_9$ and $R_{10}$ are hydrogen.

32. Process according to claim 28 further comprising the step of converting the polymer obtained in step (b).

33. Process according to claim 28, wherein the ester functions of the polymer obtained on conclusion of the stage (a) are hydrolyzed.

34. Process according to claim 28, characterized in that, prior to the stage b), the at least partially saponified polymer is crosslinked, the crosslinking taking place via at least one bridging agent and, preferably, in the presence of a coupling agent, so as to obtain a network.

35. A process as claimed in claim 34 wherein the network is of the type of those according to claim 22.

36. A process according to claim 34, wherein $R_1$ and $R_2$ are OH.

37. A process for the preparation of a polymer of formula (II):

$$\left[ \begin{array}{c} S-(CH_2)_x-CH-NH-C-R-C-NH-CH-(CH_2)_y-S \\ | \quad\quad\quad\quad || \quad\quad || \quad\quad\quad\quad | \\ C=O \quad O \quad O \quad C=O \\ | \quad\quad\quad\quad\quad\quad\quad\quad\quad\quad\quad | \\ R_1 \quad\quad\quad\quad\quad\quad\quad\quad\quad R_2 \end{array} \right]_n$$

wherein:

n is between 1 and 100;

$R_1$ and $R_2$ are identical or different and each represents $$-O-R_5;$$

$$-NH-CH-(CH_2)_z-S-R_6;$$
$$\quad\quad |$$
$$\quad COOR_7$$

or $$-NH-(CH_2)_y-S-R_6$$

wherein $R_5$, $R_6$ and $R_7$ independently represent hydrogen, and aliphatic group, an alicyclic group or an aromatic group;

R is chosen so that the radical $$-C-R-C-$$
$$|| \quad\quad ||$$
$$O \quad\quad O$$

is a residue of a polycarboxylic acid which is not citric acid; and x, y and z are each 1 or 2; in which process a product of formula (I) as claimed in claim 1 is oxidized using an oxidizing system.

38. A process for the preparation of a network comprised of polymers of formula (II) as claimed in claim 17, wherein the polymers are crosslinked by bridges resulting from at least one bridging agent.

39. A process as claimed in claim 38 wherein the bridging agents are polyols or polyamines.

40. A process as claimed in claim 37 wherein the oxidizing system comprises iodine, iodine derivatives, hydrogen peroxide or mixtures thereof.

41. A biomaterial comprised of novel organic products as claimed in claim 1, polymers obtained by oxidizing said products, networks obtained by crosslinking said polymers, or mixtures thereof.

42. A biomaterial as claimed in claim 41 which further comprises biological macromolecules or biodegradable synthetic or natural polymers.

43. Product according to claim 9 used as a biomaterial.

* * * * *